(12) United States Patent
Nakayama et al.

(10) Patent No.: US 7,527,821 B2
(45) Date of Patent: May 5, 2009

(54) SENSOR FABRICATING METHOD

(75) Inventors: Robert Nakayama, Los Angeles, CA (US); Richard Payne, Andover, MA (US); Steven Sunshine, Pasadena, CA (US); Beth Munoz, Vista, CA (US); Jing Li, Temple City, CA (US); Chang-Meng Hsiung, Irvine, CA (US)

(73) Assignee: Smiths Detection Inc., Pasadena, CA (US)

( * ) Notice: Subject to any disclaimer, the term of this patent is extended or adjusted under 35 U.S.C. 154(b) by 738 days.

(21) Appl. No.: 09/847,885

(22) Filed: May 2, 2001

(65) Prior Publication Data

US 2002/0014415 A1    Feb. 7, 2002

Related U.S. Application Data

(60) Provisional application No. 60/201,156, filed on May 2, 2000.

(51) Int. Cl.
  *B05D 5/12* (2006.01)
  *B05D 1/32* (2006.01)
  *B05D 3/02* (2006.01)
  *B05D 7/00* (2006.01)

(52) U.S. Cl. .................. 427/58; 427/123; 427/282; 427/372.2; 427/402; 427/421.1

(58) Field of Classification Search .................. 427/58, 427/123, 282, 372.2, 421, 402
See application file for complete search history.

(56) References Cited

U.S. PATENT DOCUMENTS

| | | | | |
|---|---|---|---|---|
| 3,428,892 | A | * | 2/1969 | Meinhard .................. 324/71.1 |
| 4,454,007 | A | * | 6/1984 | Pace .......................... 205/778 |
| 5,296,819 | A | * | 3/1994 | Kuroiwa et al. ............ 324/670 |
| 5,571,401 | A | * | 11/1996 | Lewis et al. .................. 205/787 |
| 5,658,443 | A | * | 8/1997 | Yamamoto et al. ..... 204/403.08 |
| 5,720,862 | A | * | 2/1998 | Hamamoto et al. ....... 205/777.5 |
| 5,756,879 | A | | 5/1998 | Yamagishi et al. ......... 73/28.01 |
| 5,945,069 | A | | 8/1999 | Buehler ....................... 422/90 |
| 6,103,033 | A | * | 8/2000 | Say et al. .................... 156/73.1 |
| 6,290,911 | B1 | * | 9/2001 | Lewis et al. .............. 422/82.02 |
| 6,450,008 | B1 | | 9/2002 | Sunshine et al. |
| 6,495,892 | B2 | | 12/2002 | Goodman et al. |
| 6,537,498 | B1 | | 3/2003 | Lewis et al. |
| 6,627,154 | B1 | | 9/2003 | Goodman et al. |
| 6,746,960 | B2 | * | 6/2004 | Goodman ................... 438/689 |
| 6,784,274 | B2 | * | 8/2004 | Van Antwerp et al. ........ 528/77 |

FOREIGN PATENT DOCUMENTS

JP    08-254520    * 10/1996

* cited by examiner

*Primary Examiner*—Brian K Talbot
(74) *Attorney, Agent, or Firm*—Foley & Lardner LLP

(57) ABSTRACT

The present invention provides methods for fabricating a sensor on a substrate having a pair of electrodes. The methods are especially amenable to broad variations amongst individual sensor on a single substrate. The intra-sensor variation within the array can be achieved in various fashions. The method provide intra-sensor variation using quantitative and qualitative differences in each sensor.

24 Claims, 5 Drawing Sheets

SENSOR FABRICATING METHOD

CROSS-REFERENCE TO RELATED APPLICATIONS

This application claims priority to U.S. Provisional Application No. 60/201,156, filed May 2, 2000, the teaching of which are hereby incorporated by reference in their entirety for all purposes.

FIELD OF THE INVENTION

This invention relates generally to sensor manufacturing and more particularly, to a novel deposition process for the fabrication of chemiresistors.

BACKGROUND OF THE INVENTION

There is considerable interest in developing chemically sensitive sensors that are capable of detecting and identifying a particular chemical analyte by a detectable response. In certain instances, these sensors are incorporated into artificial olfactory devices or electronic noses that are capable of detecting a wide variety of analytes in fluids such as vapors, gases and liquids. Typically, the electronic nose (e-nose) device comprises an array of sensors that in the presence of an analyte produces a response. The device produces a unique signature output for a particular analyte. Using pattern recognition algorithms, the output signature, such as an electrical response, can be correlated and compared to a particular analyte or mixture of substances that are known. By comparing the unknown signature with the stored or known signatures, the analyte can be detected, identified and quantified.

Certain sensor types have polymeric components. Such organic polymer-based sensors have found use in a variety of different applications and devices including, for example, devices that function as analogs of the mammalian olfactory system (see, U.S. Pat. No. 5,571,401, which issued to Lewis et al., Lundström et al., Nature 352:47-50 (1991) and Shurmer and Gardner, Sens. Actuators B 8:1-11 (1992)), bulk conducting polymer films (Barker et al., Sens. Actuators B 17:143 (1994) and Gardner et al., Sens. Actuators B 18:240 (1994)), surface acoustic wave devices (Grate et al., Anal. Chem. 67:2162 (1995), Grate et al., Anal. Chem. 65:A987 (1993) and Grate et al., Anal. Chem. 65:A940 (1993)), fiber optic micromirrors (Hughes et al., J. Biochem. and Biotechnol.41:77 (1993)), quartz crystal microbalances (Chang et al., Anal. Chim. Acta 249:323 (1991)) and dye impregnated polymeric coatings on optical fibers (Walt et al., Anal. Chem. 68:2191 (1996)).

U.S. Pat. No. 5,756,879, which issued to Yamagishi et al., on May 26, 1998, discloses a sensor comprising (a) a dielectric substrate having a surface; (b) a pair of electrically conductive electrodes disposed on the surface of the substrate; and (c) a conductive polymer covering the pair of electrically conductive electrodes, with the conductive polymer doped with appropriate dopants to change the conductive polymer from a neutral state to a charged state to provide requisite conductivity. The sensors as taught therein are limited to coating with conducting polymer sensors.

U.S. Pat. No. 5,945,069, which issued to Buehler, on Aug. 31, 1999, discloses a gas sensor test chip that utilizes a variety of electrode geometries to generate varied responses to selective gases. The gas sensor is fabricated on a substrate that includes a plurality of electrodes where each electrode has a plurality of shapes and dimensions. Polymer films are deposited over the electrodes. The polymer films have a conductivity that changes when the film is exposed to various gases as measured across the electrodes. An optimal geometric configuration for the electrode is selected based on prior tests of the film's response to various gases of interest.

WO 99/49305, published Sep. 30, 1999, discloses a method of manufacturing a batch of sensors by electrochemically depositing an active sensing material over the substrate and conductive tracks, wherein the conductive tracks are part of a single circuit, the active sensing material is then removed from a predetermined portion of the substrate and thereafter the substrate is subdivided to produce a plurality of sensors.

What is needed in the art is a process for depositing a sensor onto a substrate wherein the sensor comprises multiple layers. The present invention remedies such need.

SUMMARY OF THE INVENTION

In certain aspects, the present invention provides a method for fabricating a multi-layered sensor that is efficient and particularly amendable to fabricating sensor arrays. In certain aspects, the methods of the present invention allow for the fabrication of polymer based sensor arrays wherein the composition of each sensor is different. The variation or differentiation in the sensor array can be achieved in various fashions. In certain instances, a different polymer can be used in the fabrication of each sensor element. In other aspects, various other quantitative and qualitative differences is each sensor allow for intra-sensor variation. As such, the present invention provides a method for fabricating a sensor on a substrate having a pair of electrodes, comprising: depositing a first layer of conducting material onto the substrate having a pair of electrodes; and depositing a second layer of polymer film onto the first layer of conducting material thereby fabricating the sensor.

In certain preferred aspects, the method further comprises depositing the first and second layers through a mask. This feature facilitates the localization of multiple sensors on a single substrate thereby minimizing contamination of individual sensors within the array. In a preferred embodiment, the mask is a solid film with an aperture through which the sensor material or one component of the sensor is deposited. The size, shape and distance of the mask from the sensor substrate can be changed so that the deposited material is optimized based on the electrode configuration. The mask can be made of metal or some other non-reactive material. The mask can have multiple apertures if it is desired to deposit the same material in more than one sensor array position.

In another aspect, the present invention provides unique substrate geometries that impart advantageous properties to the sensors. These and other features, objects and advantages will become more apparent when read with the detailed description and accompanying drawings which follow.

DETAILED DESCRIPTION OF THE INVENTION AND PREFERRED EMBODIMENTS

A. Sensor Substrate

The present invention provides a method for fabricating a sensor on a substrate having a pair of electrodes, comprising: depositing a first layer of conducting material onto the substrate having a pair of electrodes; and depositing a second layer of polymer film onto the first layer of conducting material thereby fabricating the sensor.

The methods of the present invention are especially amenable to broad variations amongst individual sensors on a single substrate. The intra-sensor variation within the array can be achieved in various fashions. In a preferred embodiment, the methods provide intra-sensor variation using quantitative and qualitative differences in each sensor within the array.

Figure 1:
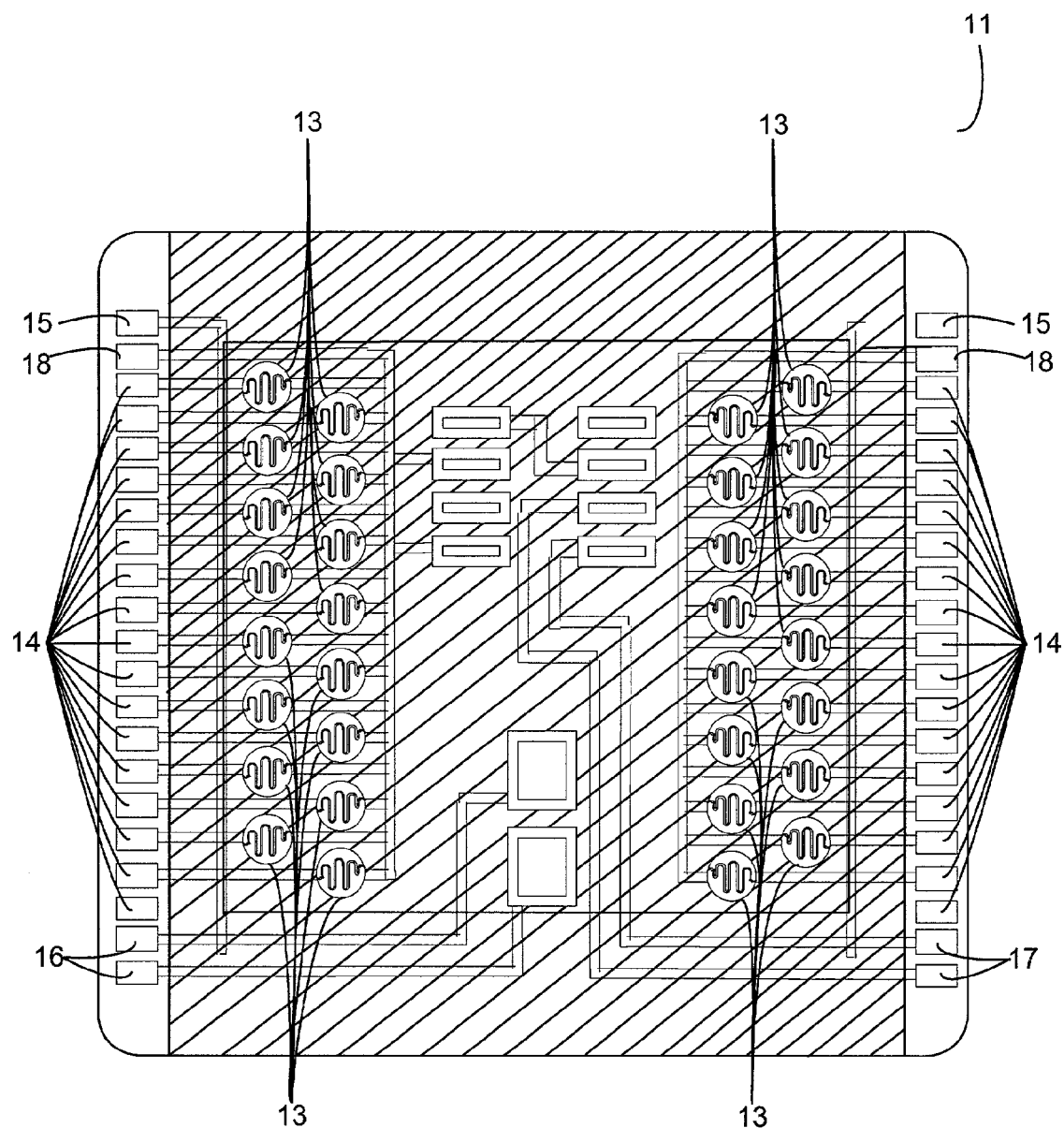
FIG. 1 shows a sensor substrate layout of the present invention.

FIG. 1 is an illustration of a sensor substrate of the present invention. This is merely one embodiment and should not limit the scope of the claims herein. One of ordinary skill in the art will recognize other variations, modifications, and alternatives.

FIG. 1 illustrates a suitable sensor substrate 11 for use in the present invention. Using methods of the present invention, the sensors are fabricated onto a substrate that includes a pair of electrodes such as a plurality of interdigitated pairs of electrodes 13, wherein each pair of electrodes can have various shapes and dimensions. The sensor substrate as shown includes contact pins 14 that allow access to sensor electrode structures such as heaters 15, thermistors 16 and relative humidity probes 17. The heaters can be used to maintain substrate temperature. Another contact pin(s) 18 is used for a ground. A contact pin 18 is connected to a common electrode in each chemiresistor or sensor. Contact pins 14 can be used to place each chemiresistor, one at a time, in the feedback loop of an operational amplifier using multiplexing test circuitry.

Figure 2:
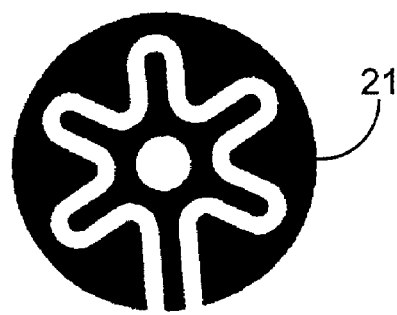
FIG. 2 shows various sensor patterns of the present invention.
Figure 2:
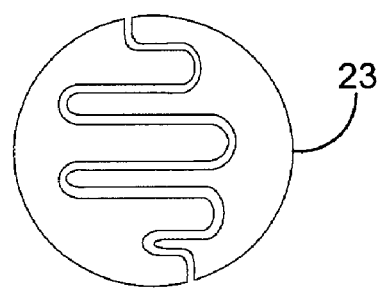
Figure 2:
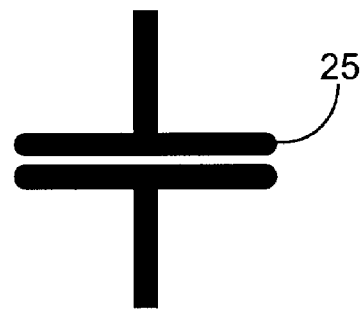
Figure 2:
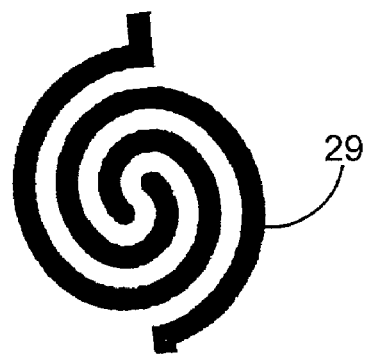

The substrate is preferably fabricated from a dielectric or insulating material such as ceramic, silicon or glass. In addition, certain substrates design configurations represent another aspect of the present invention. FIG. 2 is an illustration of various geometric configurations of sensor designs of the present invention. This is merely one embodiment and should not limit the scope of the claims herein. One of ordinary skill in the art will recognize other variations, modifications, and alternatives.

The present invention provides sensor designs that are advantageous used for various sensor arrays. For example, the star sensor configuration 21, the loop sensor configuration 23, the parallel sensor configuration 25 and the spiral sensor configuration 29 represent advancement over prior art designs. The substrate may have wells, depressions or dimples to wherein the sensing material is disposed.

The substrate optionally comprises a heater, a thermistor or a combination thereof. The thermistor is typically used to ramp up the substrate temperature to a higher temperature for more efficient sensing. Thereafter, the heater can be used to maintain the temperature at a pre-set temperature. Moreover, the substrate optional comprises a temperature probe, a humidity probe or combinations thereof. The temperature and humidity probe can be used to ascertain the sensor environmental conditions before, during and after analyte detection.

B. Process Steps

Figure 3:
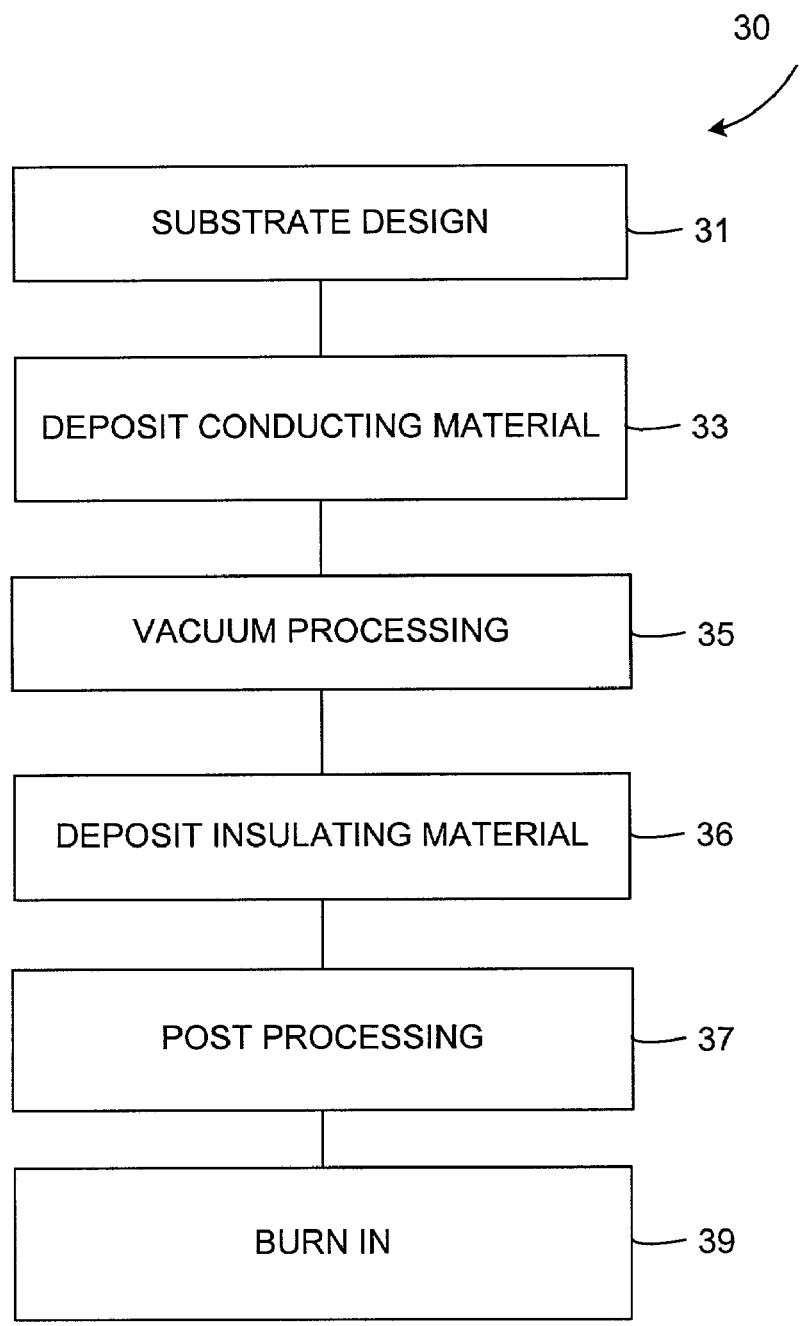
FIG. 3 shows a flow diagram of an embodiment of the present invention.

In certain embodiments, the deposition process of the present invention comprises two steps. FIG. 3 is an illustration of a flow diagram of the present invention. This is merely one embodiment and should not limit the scope of the claims herein. One of ordinary skill in the art will recognize other variations, modifications, and alternatives. FIG. 3 shows a preferred process embodiment 30 of fabricating sensors of the present invention. Initially, a substrate design is selected 31. Thereafter, a first layer of conducting material is deposited onto the substrate 33. Various conducting materials are suitable for use in the present invention. Suitable conducting materials include, but are not limited to, organic conducting materials, inorganic materials or combinations thereof. Organic conductors include, but are not limited to, conducting polymers such as poly(anilines), poly(thiophenes), poly(pyrroles), poly(acetylenes); carbonaceous materials, such as carbon blacks, graphite, coke, $C_{60}$; charge transfer complexes such as tetramethylparaphenylenediamine-chloranile, alkali metal tetracyanoquinodimethane complexes, and tetrathiofulvalene halide complexes. Those of skill in the art will know of other organic conductors suitable for use in the present invention.

Inorganic conductors include, but are not limited to, metals such as Ag, Au, Cu, Pt and metal alloys such as AuCu; highly doped semiconductors such as Si, GaAs, InP, $MoS_2$, and $TiO_2$; conductive metal oxides such as $In_2O_3$, $SnO_2$, $Na_xPt_3O_4$; superconductors such as $YB_2Cu_3O_7$, $Tl_2Ba_2Ca_2Cu_3O_{10}$. In certain preferred embodiments, the conducting material is carbon black that is commercially available from Cabot Corp, (Boston, Mass.).

Preferably, a layer of carbon black is sprayed utilizing an aerosol sprayer. The carbon black is admixed with a suitable solvent. Suitable solvents include, but are not limited to, toluene, xylene, ethanol, water and mixtures thereof. The carbon black is mixed in a solution of about 0.1% to about 5%, preferably about 0.25% to about 1% weight/weight.

In certain embodiments, the aerosol sprayer is an airbrush such as with an Intuos Airbrush, an Iwata HP-A airbrush, and the like. Preferably, the carbon black layer has a thickness between about 0.01 micron to about 10 microns. More preferably, the carbon black layer has a thickness between about 0.1 micron to about 1 micron.

The airbrush method can be adapted to robotic amateur. A number of robotic fluid transfer systems are available, or can easily be made from existing components. For example, a Zymate XP (Zymark Corporation; Hopkinton, Mass.) automated robot station using a Microlab 2200 (Hamilton; Reno, Nev.) pipetting station can be used to transfer parallel samples to a multiwell (e.g., 96 well) microtiter plates to set up several parallel simultaneous deposition processes. After the first conducting material layer has been deposited upon the substrate 33, the substrate is optionally placed into a dry box such as a desiccant box, to evaporate any excess solvent 35.

Following deposition of the first layer, a second layer, such as a polymer film layer, is deposited onto the first layer of conducting material. The polymer film layer is preferably a nonconducting or an insulating polymer 36. Suitable polymers include, but are not limited to, main chain carbon polymers, main-chain acyclic heteroatom polymers and main-chain heterocyclic polymers. Suitable examples of main-chain carbon polymers include, but are not limited to, poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes) and poly(arylenes). Suitable examples of main-chain acyclic heteroatom polymers include, but are not limited to, poly(oxides), poly(carbonates), poly(esters), poly(anhydrides), poly(urethanes), poly(sulfonates), poly(siloxanes), poly(sulfides), poly(thioesters), poly(sulfones), poly(sulfonamides), poly(amides), poly(ureas), poly(phophazenes), poly(silanes), and poly(silazanes). Suitable examples of main-chain heterocyclic polymers include, but are not limited to, poly(furan tetracarboxylic acid diimides), poly(benzoxazoles), poly(oxadiazoles), poly(benzothiazinophenothiazines), poly(benzothiazoles), poly(pyrazinoquinoxalines), poly(pyromellitimides), poly(quinoxalines), poly(benzimidazoles), poly(oxindoles), poly(oxoisoindolines), poly(dioxoisoindolines), poly(triazines), poly(pyridazines), poly(piperazines), poly(pyridines), poly(piperidines), poly(triazoles), poly(pyrazoles), poly(pyrrolidines), poly(carboranes), poly(oxabicyclononanes), poly(dibenzofurans), poly(phthalides), poly(acetals), poly(anhydrides), and carbohydrates. The present invention preferably employs polyacrylamindes, polyethylene oxide, polyvinyl alcohol, polystyrene and derivatives thereof as the polymer film layer.

In certain aspects, different polymers are used to generate intra-sensor variation within the sensor array. For instance, in one embodiment, 32 different polymers are used to generate a 32 sensor array. In certain other instances, a 32 sensor array can be generated with just 3 or 4 polymers using different polymer concentrations. The present invention encompasses all such variations.

In one embodiment, fabrication of the sensors occurs in an environment wherein air flow is reduced or static. For instance, if the fabrication is occurring in a chemical hood, the air venting system is turned off, or a zero air flow is maintained in the hood. In certain aspects, in order to achieve uniform deposition of a carbon black layer during the deposition of a first layer onto the substrate, the airflow is reduced or eliminated.

After the polymer is deposited, the sensor is optionally post processed 37. This process step depends on the polymer type. In certain instances during post processing, the polymer is cross-linked, cured, photopolymerized, and the like. Thereafter, the sensor or sensor array can be optionally burned in 39. In this process, the sensor(s) is exposed to one or more solvents in order to condition the sensor(s). This exposure to one or more solvents can be repeated multiple times.

In certain aspects, the burn in process is used to speed up the relaxation of a polymer-carbon black composite to its lowest free energy level. Meanwhile, a solvation process also occurs to generate a stable chemical environment for the sensor(s). In one embodiment, during the burn in process the sensor(s) (e.g., polymer-carbon black composites) are exposed to non-polar (e.g., toluene) and polar (e.g., methanol) at their saturated vapor concentrations in cycles (vapor exposure and air purge) over time (e.g., 48 hours) at room temperature. Since the materials swell during the vapor exposure and contract during the air purge, the extensive vapor exposures at high concentration of two solvents speeds up the relaxation.

In certain aspects, the polymer film is prepared using combinatorial techniques. WO 99/00663, published Jan. 7, 1999, and incorporated herein by reference, discloses polymer based sensors prepared using combinatorial techniques. As described therein, sensors are prepared using various ratios of at least first and second organic material which when combined form a polymer blend that is capable of absorbing a chemical analyte thereby providing a detectable response.

Moreover, in other aspects, the polymers used in the fabrication methods of the present invention can be used to separate enantiomers. WO 99/40423, published Aug. 12, 1999, and incorporated herein by reference, discloses compositionally different sensors having a chiral region. The polymers described therein can be used in the fabrication methods of the present invention.

In addition, European Patent Application No. 0 794 428, published Sep. 10, 1997, describes sensors capable of distinguishing between enantiomers. The sensor comprise a pair of spaced apart contacts and a conducting polymer material spanning the gap. The polymer has chiral sites in the polymer material formed by incorporating optically active counter ions such as camphor sulfonic acid. The polymer material can be used in the methods of the present invention.

In certain other aspects, the present invention relates to polymers have small molecules of low volatility incorporated therein. WO 99/67627, published on Dec. 29, 1999, and incorporated herein by reference, discloses plasticized polymers that can be used in the fabrication methods of the present invention.

In still yet another aspect, the polymers used in the methods of the present invention are disclosed in U.S. application Ser. No. 09/201,999, filed Dec. 1, 1998, now abandoned, incorporated herein by reference. As described therein, the sensor arrays for detecting an analyte in a fluid comprise first and second sensors wherein the first sensor comprises a region of aligned conductive material; electrically connected to an electrical measuring apparatus. The aligned conductive material improves the signal to noise of vapor sensors allowing lower detection limits. Lower detection limits allow for the identification of lower concentrations of hazardous material and is advantageous in medical applications, such as the detection of disease states.

The formation of a film of a polymer disposed on a conducting layer having at least one pair of electrodes thereon can be effected by various methods, for example, a method wherein a solution of a conductive polymer is prepared and then coated by, for example, spin coating, dipping, drop coating, roll coating or the like, a vapor deposition method (e.g. vacuum deposition), a plasma polymerization method or the like. In certain aspects, the polymer film is electrochemically deposited resulting in uniform thin films with strong adhesion.

In another embodiment, sensors of the present invention can be coated with a thin layer of chemically selective material providing highly responsive chemical sensors for the detection and monitoring of vapors and gases using a thin film deposition technique such as matrix assisted pulsed laser evaporation (MAPLE) and MAPLE-Direct Write (MAPLE-DW). In a preferred aspect, the MAPLE technique is used to coat high quality polymer films on SAW devices, and conventional pulsed laser deposition is used to deposit a passivation layer of diamond-like-carbon on a SAW device surface to prevent water adsorption. (see, R. Andrew McGill, et al., *IEEE Transactions on Ultrasonics, Ferroelectrics, and Frequency Control* 45:1370-1380 (1998)). Those skilled in the art will know of other deposition techniques suitable for use in fabricating sensors of the present invention.

The suitable thickness of conductive polymer can differ depending upon the type of the substance, etc. but is generally 0.1-100 microns, preferably 1-20 microns, and more preferably about 1 to about 10 microns. The solution of the conductive polymer can contain, as necessary, a film-formable polymer, plasticizers, chiral fillers, etc. The thickness of the polymer coating must be sufficient to cover the conducting layer, but not so thick as to crack.

The polymer is preferably admixed into an appropriate solvent. Suitable solvents include, but are not limited to, toluene, tetrahydrafuran, acetone, and methylethylketone. The polymer is mixed in a solution of about 0.1% to about 5%, preferably about 0.25% to about 1% weight/weight. The deposition of the polymer film can be accomplished by any suitable means. In a preferred embodiment, the deposition process is automated using robotic armature. One suitable device is a BIOMEK 2000 available from Beckman-Coulter Corp. After the polymer is deposited, the sensor is optionally post processed 37. This process step depends on the polymer type. In certain instances during post processing, the polymer is cross-linked, cured, photopolymerized, and the like.

In certain preferred embodiments, the sensor fabrication methods of the present invention are used to manufacture arrays of sensors. Preferably, the fabrication methods relate to deposition of an array of compositionally different sensors on a single substrate. In order to localize the different sensors to the confined area between one set of electrodes and minimize contamination and subsequent communications between independent sensors, a shadow mask is optionally employed during fabrication.

In a preferred aspect, during the manufacture of an array of different sensors on a single substrate, a shadow mask is employed. Preferably a 2-mask process is used. The shadow mask is a solid film with an aperture or a plurality of apertures, through which the sensor material or one component of the sensor is deposited. The size, shape and distance of the mask from the sensor substrate can be changed so that the deposited film size and shape is optimized based on the electrode configuration. The mask can be made of metal or some other non-reactive material. The mask can have multiple apertures if it is desired to deposit the same material in more than one array position.

Figure 4:
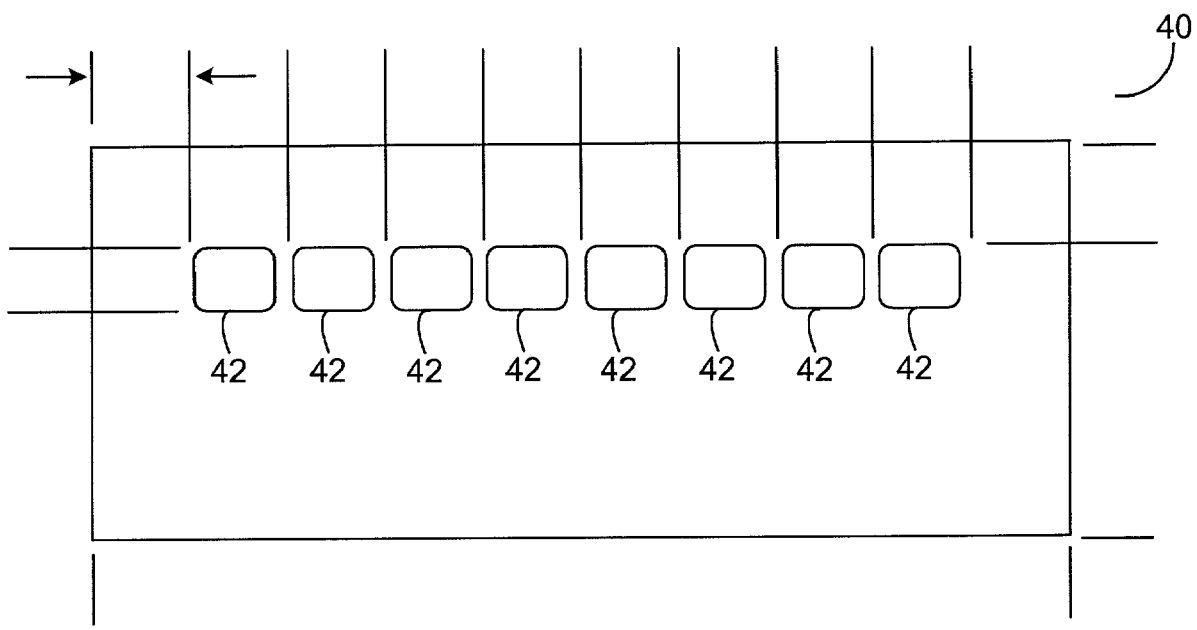
FIG. 4 shows one embodiment of a deposition mask of the present invention.

FIG. 4 is an illustration of one embodiment of a shadow mask of the present invention. This is merely one embodiment and should not limit the scope of the claims herein. One of ordinary skill in the art will recognize other variations, modifications, and alternatives.

FIG. 4 shows a shadow mask 40 of the present invention. In a preferred embodiment, the first layer of conducting material is deposited through apertures 42 in order to make uniform regions of conducting material and minimize contamination between sensors. In a preferred embodiment, the shadow mask is about 0.00001 inch to about 0.01 inch thick. More preferably, the mask is about 0.0001 to about 0.0008 inches thick. The mask preferably comprises polypropylene with a plurality of appertures.

Figure 5:
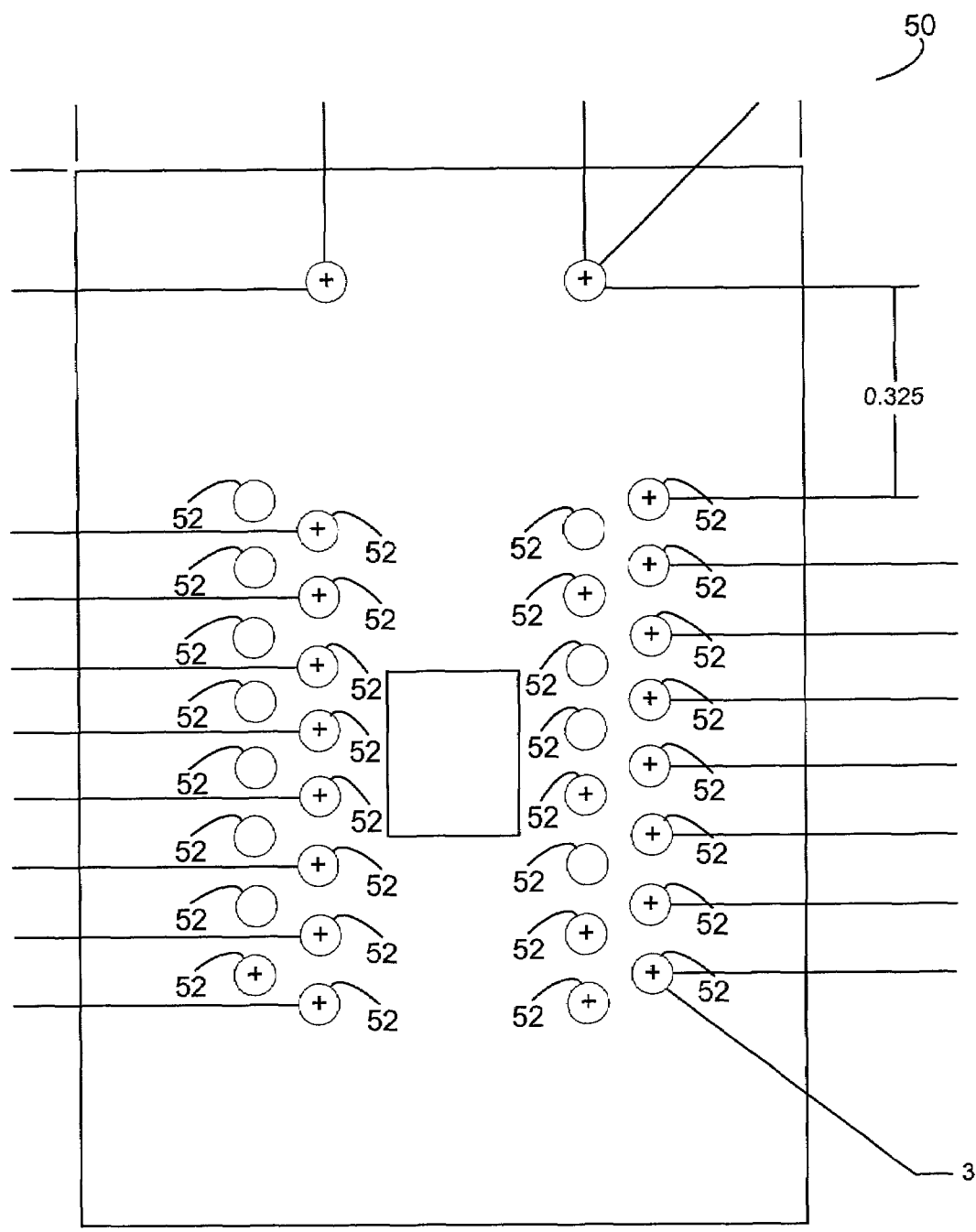
FIG. 5 shows one embodiment of a deposition mask of the present invention.

FIG. 5 is an illustration of a shadow mask embodiment of the present invention. This is merely one embodiment and should not limit the scope of the claims herein. One of ordinary skill in the art will recognize other variations, modifications, and alternatives.

FIG. 5 shows one embodiment of a shadow mask 50 of the present invention. In a preferred embodiment, the second layer of nonconductive material is deposited through apertures 52 in order to make uniform regions of polymer material and minimize contamination between sensors. In a preferred embodiment, the shadow mask is about 0.00001 inch to about 0.01 inch thick. More preferably, the mask is about 0.0001 to about 0.0008 inches thick. The mask preferably comprises polypropylene.

In a further embodiment, the present invention provides a system that automatically moves the mask and/or the substrate so that different sensor elements can be deposited without having to remove masks between each deposition. In one aspect, a multiple head spraying device is used wherein each head can deposit a different sensor composition. A mask is constructed that has at least one aperture and this aperture (or apertures) is moved into position automatically using an x, y, and z translational stage so that the appropriate spraying apparatus can spray a sensor onto a substrate. In this manner, two sensor arrays (four elements each) are manufactured at the same time by using a mask with two openings. The first element on each substrate is deposited and then the mask is translated and the second sensor is deposited on each substrate. The system automatically deposits many sensors by choosing the spray head and translating the mask to the appropriate position.

C. Sensor Systems

The sensors fabricated using the present methods are preferably incorporated into electronic olfaction devices as described in WO 99/47905 and U.S. Pat. No. 6,085,576. As described therein, a handheld sensing apparatus is provided that includes a housing, a sensor module, a sample chamber, and an analyzer. The sensor module and the analyzer mount in the housing. The sensor module includes at least two sensors that provide a distinct response to a particular test sample. The sample chamber is defined by the housing or the sensor module, or both, and incorporates an inlet port and an outlet port. The sensors are located within or adjacent to the sample chamber. The analyzer is configured to analyze a particular response from the sensors and to identify or quantify, based on the particular response, analytes within the test sample.

Analytes detectable by the sensors fabricated using methods of the invention include, but are not limited to, alkanes, alkenes, alkynes, dienes, alicyclic hydrocarbons, arenes, alcohols, ethers, ketones, aldehydes, carbonyls, carbanions, heterocycles, polynuclear aromatics, organic derivatives, biomolecules, microorganisms, bacteria, viruses, sugars, nucleic acids, isoprenes, isoprenoids, and fatty acids and their derivatives. Many biomolecules, such as amino acids, and nucleic acid are amenable to detection using the sensor arrays of the invention.

The sensors fabricated using methods of the present invention can be used to enable medical and dental care-providers to quickly and accurately identify the chemical components in breath, wounds, and bodily fluids to diagnose a host of illness including infections and metabolic problems. For example, the sensors can be used to test for skin conditions, for anesthesia administration, or to determine time of ovulation in fertility treatment. Alternatively, the sensors fabricated using methods of the present invention can classify and identify microorganisms, such as bacteria.

The sensors fabricated using methods of the present invention can be used to locate an odor to identify a complicated system or state of matter, and can offer versatility and reliability absent from conventional environmental or chemical monitoring devices. Advantageously, the sensors fabricated using methods of the present invention can be used for profiling a chemical environment in a hazardous materials situation and to assist emergency crews to accurately select fire retardant, containment strategies, and protective gear.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A method for fabricating an olfactory sensor on a substrate having a pair of electrodes, said method comprising:
   a) depositing at least one conducting material as a first layer onto said substrate having a pair of electrodes, the first layer being capable of sensing a chemical analyte that contacts the first layer;
   b) depositing at least one non-conductive or insulating film that is capable of absorbing the chemical analyte that is provided thereon as a second layer, onto said first layer of conducting material, thereby fabricating said sensor; and
   c) post-processing said second layer after depositing upon said first layer of conducting material, in order to burn-in the olfactory sensor,
   wherein said olfactory sensor is comprised of at least one sensor composition, and
   wherein the chemical analyte is absorbed within the second layer so as to make contact with the first layer; and
   wherein the post-processing comprises:
      exposing the second layer to either a non-polar substance or a polar substance,
      wherein the exposing step is performed in cycles over a predetermined time period.

2. The method according to claim 1, wherein said conducting material comprises carbon black.

3. The method according to claim 1, wherein said deposition of said conducting material is by aerosol spraying.

4. The method according to claim 2, further comprising drying said carbon black before deposition of said second layer.

5. The method according to claim 2, wherein said carbon black layer has a thickness between about 0.01 micron to about 10 microns.

6. The method according to claim 5, wherein said carbon black layer has a thickness between about 0.1 micron to about 1 micron.

7. The method according to claim 1, further comprising depositing said first layer of conducting material through a mask.

8. The method according to claim 7, wherein said mask comprises a plurality of apertures.

9. The method according to claim 1, wherein said deposition of said first layer of conducting material comprises robotic amateur.

10. The method according to claim 1, wherein said deposition of said second layer comprises robotic amateur.

11. The method according to claim 1, further comprising depositing said second layer through a mask.

12. The method according to claim 11, wherein said mask comprises a plurality of apertures.

13. The method according to claim 1, wherein said post-processing is selected from the group consisting of vacuum processing, photoactive polymerization and cross-linking.

14. The method according to claim 1, wherein said sensor is an array of sensors having a first sensor composition and a second sensor composition, the method further comprising:
   forming at least one sensor in the array of sensors to have a star-shaped configuration and forming at least another sensor in the array of sensors to have a spiral-shaped configuration.

15. The method according to claim 14, wherein said first sensor is compositionally different than said second sensor composition.

16. The method according to claim 14, wherein said first sensor composition has a different polymer film layer than said second sensor composition.

17. The method according to claim 1, wherein said substrate comprises a dielectric material.

18. The method according to claim 1, wherein said substrate further comprises a member selected from the group consisting of a heater, a thermistor and a combination thereof.

19. The method according to claim 1, wherein said substrate further comprises a member selected from the group consisting of a temperature probe, humidity probe and a combination thereof.

20. The method according to claim 1, wherein the exposing step comprises:
   exposing the second layer to both the non-polar substance and the polar substance at respective saturated vapor concentrations for the non-polar substance and the polar substance,
   wherein the exposing step is performed at room temperature.

21. A method for fabricating an olfactory sensor on a substrate having a pair of electrodes, said method comprising:
   a) depositing a first layer of conducting material onto said substrate having a pair of electrodes to form a substrate having a conducting material disposed thereon, the first layer being capable of sensing a chemical analyte that contacts the first layer;
   b) drying said substrate having a conducting material disposed thereon to remove any solvent;
   c) depositing a second layer of non-conductive or insulating film that is capable of absorbing the chemical analyte that is provided thereon, onto said first layer of conducting material, to form a fabricated sensor; and
   d) post-processing said fabricated sensor to cure said second layer,
   wherein the chemical analyte is absorbed within the second layer so as to make contact with the first layer,
   wherein the post-processing comprises:
      exposing the second layer to either a non-polar substance or a polar substance,
      wherein the exposing step is performed in cycles over a predetermined time period.

22. The method according to claim 21, wherein said sensor is an array of sensors.

23. The method according to claim 21, wherein said sensor is an array of sensors having a first sensor composition and a second sensor composition, and wherein the method further comprises:
   forming at least one sensor in the array of sensors to have a star-shaped configuration and forming at least another sensor in the array of sensors to have a spiral-shaped configuration.

24. The method according to claim 21, wherein the exposing step comprises:
   exposing the second layer to both the non-polar substance and the polar substance at respective saturated vapor concentrations for the non-polar substance and the polar substance,
   wherein the exposing step is performed at room temperature.

* * * * *